United States Patent [19]
McCluney

[11] 4,053,229
[45] Oct. 11, 1977

[54] 2°/90° LABORATORY SCATTERING PHOTOMETER

[75] Inventor: William R. McCluney, Greenbelt, Md.

[73] Assignee: The United States of America as represented by the Administrator of the National Aeronautics and Space Administration, Washington, D.C.

[21] Appl. No.: 648,700

[22] Filed: Jan. 13, 1976

[51] Int. Cl.² .......................................... G01N 21/00
[52] U.S. Cl. ................................. 356/103; 356/104
[58] Field of Search ............... 356/103, 104, 208, 201, 356/205

[56] References Cited
U.S. PATENT DOCUMENTS

| 3,310,680 | 3/1967 | Hasegawa | 356/104 |
| 3,518,439 | 6/1970 | Fuhrmann | 356/208 |
| 3,659,946 | 5/1972 | Kozawa et al. | 356/208 |
| 3,664,752 | 5/1972 | Hermieu | 356/208 |
| 3,710,933 | 1/1973 | Fulwyler et al. | 356/104 |
| 3,756,726 | 9/1973 | Astheimer | 356/205 |
| 3,785,735 | 1/1974 | Friedman et al. | 356/103 |
| 3,800,147 | 3/1974 | Shea et al. | 356/208 |

FOREIGN PATENT DOCUMENTS 2,409,273  4/1975  Germany ................. 356/103

Primary Examiner—John K. Corbin
Assistant Examiner—R. A. Rosenberger
Attorney, Agent, or Firm—John O. Tresansky; Robert D. Marchant; John R. Manning

[57] ABSTRACT

A scattering photometer for measuring the light scattered by particles in a hydrosol at substantially 2° and 90° simultaneously. Light from a source is directed by a first optical system into a scattering cell containing the hydrosol under study. Light scattered at substantially 90° to the incident beam is focused onto a first photoelectric detector to generate an electrical signal indicative of the amount of scattered light at substantially 90°. Light scattered at substantially 2° to the incident beam is directed through an annular aperture symmetrically located about the axis of the illuminating beam which is linearly transmitted undeviated through the hydrosol and focused onto a second photoelectric detector to generate an electrical signal indicative of the amount of light scattered at substantially 2°.

13 Claims, 5 Drawing Figures

2°/90° LABORATORY SCATTERING PHOTOMETER

ORIGIN OF THE INVENTION

The invention described herein was made by an employee of the United States Government and may be manufactured and used by or for the Government for governmental purposes without the payment of any royalties thereon or therefor.

BACKGROUND OF THE INVENTION

1. Field of the Invention:

The present invention relates to light scattering photometers for making multiple measurements simultaneously and, more particularly, to apparatus permitting the simultaneous measurement of light at two different angles in a photometer.

2. Description of the Prior Art:

Inhomogeneity in the indices of refraction of particulates in natural waters leads to scattering of an incident beam of light, the intensity of the scattered light varying with its angular relationship to the optical axis of the incident beam. It has been found that particulates present in sea water having a high index of refraction, substantially 1.15 relative to water, characteristic of inorganic materials such as silica or calcium carbonate and organic skeletal material, tend to scatter light at large angles, greater than 80°. On the other hand, particulates in sea water having a low index of refraction, 1.01 to 1.05 relative to water, characteristic of organic material, play a strong role in the scattering of light at smaller angles, 1° to 10°. These results suggest that a scattering photometer capable of simultaneously observing the light scattered at a small angle of scattering, 1° to 10°, and at a large angle of scattering, greater than 80°, could distinguish between the low and high index particulate matter present in natural waters and industrial streams.

Known prior art scattering phtometers are incapable of simultaneous measurement of light scattered at both a small angle of scattering and a large angle of scattering. Additionally, they are incapable of continuous operation while a liquid suspension or hydrosol is being pumped through the scattering cell, as would be the case for example, if the photometer were operated aboard a ship underway. Furthermore, these instruments are large and bulky and incapable of considerable miniaturization.

BRIEF SUMMARY OF THE INVENTION

It is therefore one object of the present invention to provide a scattering photometer which is able to measure both small and large angle scatterings simultaneously.

It is another object of the present invention to provide such a scattering photometer which is small, compact, and can be operated continuously while a sample stream of water flows through the scattering cell.

It is yet another object of the present invention to provide such a scattering photometer which, with suitable calibration and use of appropriate formulas, can be used to determine the volume concentration of organic and inorganic, including organic skeletal, particulates present in a stream of water flowing through the scattering cell.

The objects of the present invention are achieved by a photometer for measuring the light scattered by particles in a hydrosol at substantially 2° and substantially 90° simultaneously. The photometer comprises a body having a passage for receiving the hydrosol, a light source, and first optical means for directing light of the source toward the hydrosol in the passage as an incident beam having an optical first axis. The photometer further includes a first photoelectric detector and a second optical means having an optical second axis at an angle of substantially 90° relative to the first axis through their point of intersection which directs light of the beam scattered by the hydrosol onto the first photoelectric detector. A second photoelectric detector and third optical means are provided, the third optical means having an aperture and directing light of the beam scattered by the hydrosol onto the second photoelectric detector, the axis of the portion of the incident beam linearly transmitted by the hydrosol and the rays of the incident beam scattered through the aperture defining an angle of substantially 2°. The photometer further comprises a light trap for absorbing the light linearly transmitted by the hydrosol, and means in circuit with each of the photoelectric detectors for providing an indication of the amount of light directed toward each detector by the associated optical means.

The foregoing, as well as other objects, features and advantages of the present invention will become more apparent from the following detailed description taken in conjunction with the appended drawings.

DESCRIPTION OF THE PREFERRED EMBODIMENTS

Figure 1:
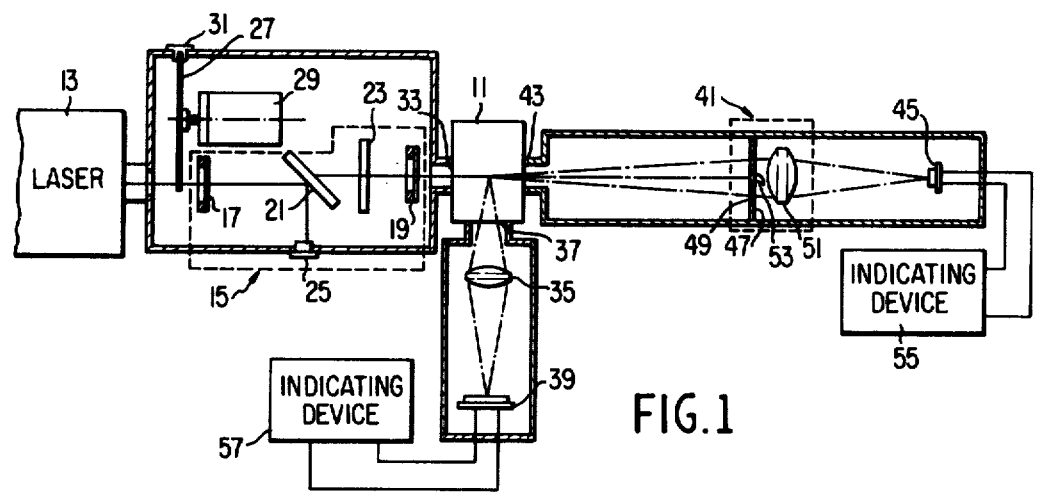
FIG. 1 is a horizontal cross sectional view of a first embodiment of the 2°/90° laboratory scattering meter in accordance with the present invention.

Referring now to the drawings, wherein like reference numerals designate identical or corresponding parts, there is shown in FIG. 1 a diagram of a first embodiment of the 2°/90° scattering photometer.

The scattering cell 11 is a body having a passage containing the hydrosol under study. Light emitted by a laser light source 13 is directed by an optical system 15 as an incident beam having an optical axis intercepting the passage in the scattering cell 11. The optical system 15 comprises the pinhole spatial filters 17 and 19, the beam splitter 21, the calibrated neutral density filter 23 and the laser output monitoring detector 25. A chopper wheel 27 driven by a synchronous motor 29 is interposed between the light source 13 and the optical system 15 to interrupt periodically the emitted light. A light-source detector pair 31 is positioned to direct another beam of light through the chopper wheel 27 to provide a reference signal for use in the synchronous detection of the laser light scattered by the hydrosol passing through the scattering cell 11. The laser light beam emerging from the chopper wheel 27 passes through the pinhole spatial filter 17 onto the beam splitter 21. The pinholes 17 and 19 serve to prevent stray scattered light and multiply-reflected light from reaching the scattering cell 11. The beam splitter 21, an uncoated optical glass interposed between the pinhole spatial filter 17 and the calibrated neutral density filter 23 directs a small portion of the light from the source onto the laser output monitoring detector 25 while permitting most of the light to pass through the beam splitter 21 and then through the calibrated neutral density filter 23 into the spatial pinhole filter 19. The light emerging from the spatial pinhole filter 19 passes in the front window 33 of the scattering cell 11 into the hydrosol to be tested. The calibrated neutral density filter 23 permits reduction of the incident beam irradiance by an accurately known amount to prevent saturation of the photoelectric detectors used in the detection of the laser light scattered by the hydrosol.

Although the above description of the first optical system is preferred, it should be understood that many other conventional optical devices may be used in order to direct the light beam into the hydrosol flowing through the passage in the scattering cell 11.

The hydrosol will scatter light in all directions, but the intensity of the scattered light will vary with its angular relationship to the optical axis of the incident beam. A second optical system comprising a focusing lens 35 is arranged to receive light scattered through the window 37 in the side of the scattering cell 11 and directed on a photoelectric detector 39, preferably a silicon diode, which generates an electrical signal commensurate with the intensity of the scattered light received. The optical axis of the focusing lens 35 defines an angle of substantially 90° relative to the optical axis of the incident beam, and the focusing lens is spaced from the incident beam in accordance with the formula $$1/S_1 + 1/S_2 = 1/f$$

where $S_1$ is the distance from the lens 35 to the incident beam, $S_2$ is the distance fom the lens 35 to the detector 39, and $f$ is the focal length of the lens 35, thus, insuring that the scattering volume of light is focused at the proper magnification on detector 39. A third optical system 41 is arranged to receive light scattered through the window 43 in the rear of the scattering cell 11 and to direct it on a second photoelectric detector 45. The third optical system 41 comprises a radiant energy mask 47 spaced from the point of intersection in the direction of the axis of the incident beam away from the light source 13 and having an annular aperture 49 for projecting a cone or portion thereof of the scattered light onto the focusing lens 51 for imaging at the second photoelectric detector 45, preferably a silicon diode. The spacing of radiant energy mask 47 and focusing lens 51 is arrived at in the same manner as the spacing of focusing lens 35. The light of the beam linearly transmitted by the hydrosol in the scattering cell 11 in the direction of the axis of the aperture 49 is largely absorbed in a light trap 53 located on or near the radiant energy mask 47. The light trap is a bent cone-shaped container having one open side and black internal walls. The annular aperture is symmetrically located about the axis of the portion of the laser beam linearly transmitted by the hydrosol, the axis and the rays of the incident beam scattered through the aperture defining an angle of substantially 2°. The photoelectric detectors are connected in circuit with separate indicating devices 55 and 57, each equipped with a galvanometer from which the amount of light received by the associated photoelectric detector can be read using synchronous detection techniques which are well known to those skilled in the art.

Figure 2:
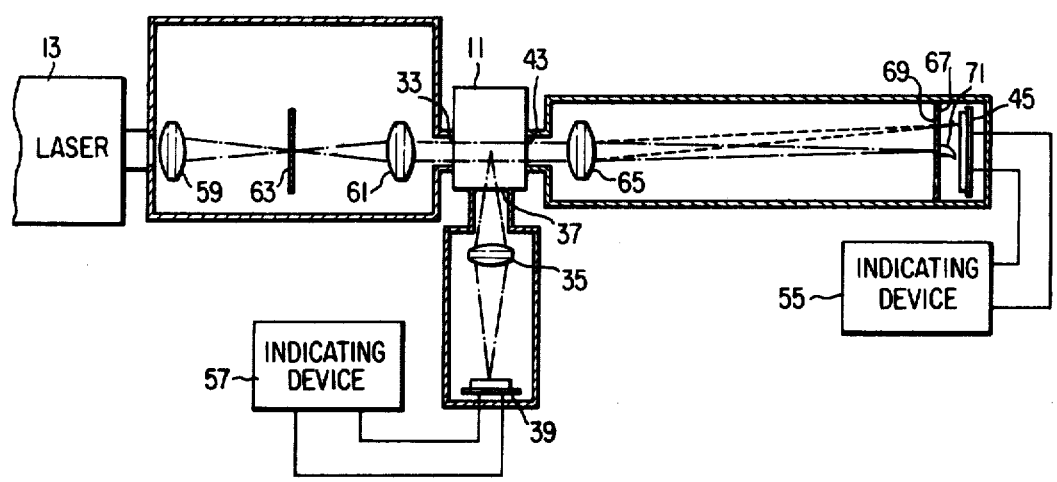
FIG. 2 is a horizontal cross sectional view of a second embodiment of the 2°/90° laboratory scattering meter in accordance with the present invention.

A second embodiment of the 2°/90° scattering photometer is illustrated in FIG. 2. It differs from the device described above by the removal of the chopper wheel 27 and light source detector pair 31 and by the substitution for the first optical system 15 of the microscope objective lens 59, the collimating lens 61, and the pinhole spatial filter 63 for directing light of the source passing through the microscope objective lens onto the collimating lens, and thence to the hydrosol under study. In addition, the third optical system 41 has been replaced by the focusing lens 65, and the mask 67 at its focal plane having an annular aperture 69 for permitting a cone of the scattered light to be incident onto the second photoelectric detector 45, now disposed directly behind the mask. As before, light of the beam linearly transmitted by the scattering cell in the direction of the axis of the aperture is largely absorbed in a light trap 71, or, if desired, it may be transmitted through a hole located in the center of the detector 45 to a light trap located behind the detector 45.

Supporing structure and other conventional elements have been omitted from FIGS. 1 and 2, and the elements illustrated will be recognized by those skilled in the art as representative of several types of elements that can be used. Thus, the laser 13 can be replaced by a small source of light, as for example, a General Electric No.1649 filament lamp and collimating lens, and the focusing lens 35 can be replaced by a baffled tube.

Figure 3:
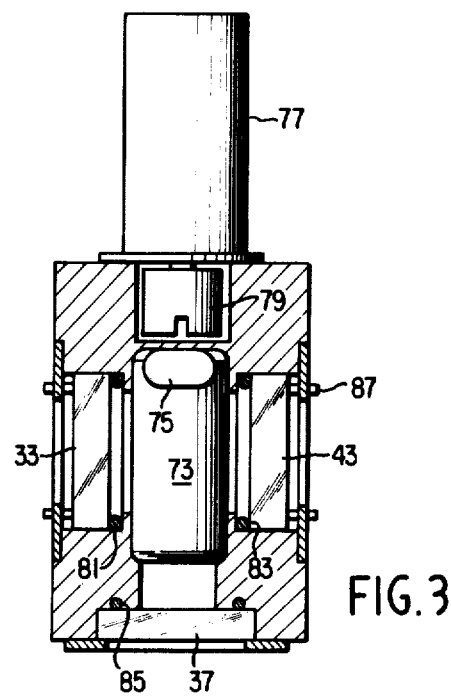
FIG. 3 is a horizontal cross sectional view of the scattering cell.

FIG. 3 illustrates a horizontal cross sectional view of the scattering cell 11. The passage 73 permits the hydrosol under study to pass through the scattering cell in the vertical direction. A stirring magnet 75 activated by the motor 77 and driving magnet 79 agitates the hydrosol. The front, rear and side windows, 33, 43 and 37 are provided to permit light to pass through the scattering cell 11 and are pressure fitted against the seals 81, 83 and 85 by means of window adjustment screws 87, which also serve as a means for proper alignment of the windows with respect to the illuminating beam.

Figure 4:
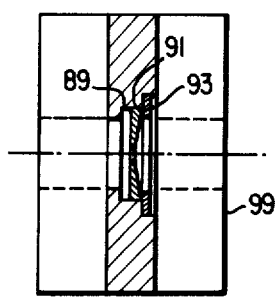
FIG. 4 is a horizontal cross sectional view of the 2° calibration reference cell.
Figure 5:
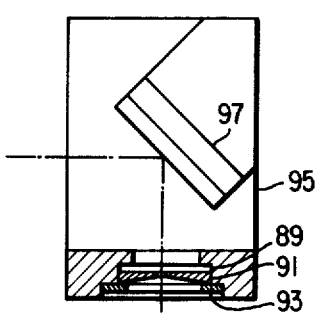
FIG. 5 is a horizontal cross sectional view of the 90° calibration reference cell.

In order to calibrate the 2°/90° scattering meter, the calibration reference cells shown in horizontal cross section in FIGS. 4 and 5 respectively are substituted for the scattering cell 11. In both cases, light from the laser 13 in incident on the center of a disc-shaped opal glass diffuser 89. A pinhole aperture 91 fits snugly against the diffuser to select a portion of the central bright spot of the diffuser having approximately uniform radiance. A retainer ring 93 maintains the diffuser and pinhole aperture in place. In the 90° reference cell 95 of FIG. 5 a mirror 97 is provided to reflect the laser beam onto the center of diffuser. The edges of the pinholes of the apertures are wafer thin to minimize edge effects. The pinholes approximately match the diameter of the laser beam. Thus, when the 2° reference cell 99 is in place the lens 51 forms an image of the 2° diffuser pinhole which is approximately the same size as the image of the scattering volume on the detector 45 when the scattering cell 11 is used. The diameter of the 2° photoelectric detector 45 is chosen to be approximately 10–20% larger than the images of the calibration diffuser pinhole and the scattering volume. When the 90° reference cell 95 is in place, the lens forms an image on the 90° photoelectric detector 39 of the illuminated portion of the scattering medium within the cell. This image has the shape of a long, thin rectangle. The 90° detector diameter is approximately seven times the width of this image.

When the scattering cell 11 is replaced by the 90° reference cell 95, an out-of-focus image of the diffuser 89 and pinhole 91 falls on the detector 39. This arrangement spreads the light from the diffuser over a larger area of the detector than would be the case if the image were in focus and thereby minimizes errors due to nonuniformity of response over the detector area.

In operation, the 2°/90° scattering meter is first calibrated by substituting the calibration reference cells for the scattering cell and measuring the signal output of the 2° detector with the 2° calibration reference cell in place, and the output of the 90° detector with the 90° calibration reference cell in place. The calibration reference cells are then removed and the scattering cell is replaced in the scattering meter. The volume scattering functions in the 2° and 90° directions or the volume concentration of the scatterers can then be determined directly from the measured detector signals by use of appropriate formulas.

Obviously, numerous additional modifications and variations of the present invention are possible in light of the above teachings. It is therefore to be understood that within the scope of the appended claims the invention may be practiced otherwise than as specifically described herein.

What is claimed as new and desired to be secured by letters patent is:

1. A photometer for measuring the light scattered by particles in a hydrosol at substantially 2° and substantially 90° simultaneously, comprising:
    a body having a passage for receiving the hydrosol;
    a light source;
    rotatable chopper means axially aligned with the light of said source for periodically interrupting said light;
    first optical means for directing the light passed through said chopper means toward the hydrosol in the passage as an incident beam having an optical first axis;
    light source detector means surrounding a portion of the outer periphery of said chopper means and emitting another beam of light through said chopper means and detecting the same for providing a reference signal to synchronously detect the light scattered by the hydrosol;
    a first photoelectric detector;
    second optical means for directing the light of the beam scattered by the hydrosol in the passage onto said first photoelectric detector and for thereby causing said first photoelectric detector to generate an electrical signal indicative of the amount of the scattered light;
    said second optical means having an optical second axis defining an angle of substantially 90° relative to the first axis, said second optical means being spaced from the first axis;
    a second photoelectric detector;
    third optical means having a radiant energy mask with an aperture for directing light of the incident beam scattered by the hydrosol in the passage toward said second photoelectric detector, the axis of the portion of the incident beam linearly transmitted by the hydrosol in the passage and the rays of the incident beam scattered through the aperture of said radiant energy mask defining an angle of substantially 2°;
    a light trap spaced from the point of intersection in the direction of the first axis away from said light source for absorbing the light of said source linearly transmitted by the hydrosol in the passage; and
    means in circuit with each of said photoelectric detectors for producing an indication of the amount of light directed towards said photoelectric detectors by the associated optical means respectively.

2. The photometer recited in claim 1 wherein: said light source is a laser.

3. The photometer recited in claim 2 wherein said first optical means includes:
    a calibrated neutral density filter;
    a laser output monitoring detector;
    a first pinhole spatial filter for passing the light from said source;
    a second pinhole spatial filter;
    a beam splitter interposed between said first pinhole spatial filter and said calibrated neutral density filter for directing a small portion of the light from said source onto said laser output monitoring detector while permitting a portion of the light of said source to pass through said calibrated neutral density filter onto said second spatial pinhole filter.

4. The photometer recited in claim 1 wherein said first optical means includes:
    a microscope objective lens;
    a collimating lens; and
    a pinhole spatial filter for directing light of said source passing through said microscope objective lens onto said collimating lens.

5. The photometer recited in claim 1 wherein: said second optical means is a focusing lens.

6. The photometer recited in claim 1 wherein: said second optical means is a baffled tube.

7. The photometer recited in claim 1 wherein: the aperture of said third optical means is annular and symmetrically located about the axis of the portion of the incident beam linearly transmitted by the hydrosol in the passage.

8. The photometer recited in claim 1 wherein: said first photoelectric detector and said second photoelectric detector are silicon diodes.

9. The photometer of claim 1 wherein said body includes:
    a first transparent window in axial alignment with said optical first axis;
    a second transparent window axially spaced from said first window and in axial alignment with said optical first axis forming said passage for said hydrosol;
    a third transparent window transverse to and spaced from said optical first axis; and
    means for agitating said hydrosol within said passage for maintaining uniform consistency within said hydrosol.

10. The photometer of claim 9 wherein said agitating means includes:
    a stirring magnet within said passage;
    a driving magnet spaced from and in axial alignment with and magnetically coupled to said stirring magnet through a portion of said body disposed between said stirring and said driving magnet; and
    motor means coupled to said driving magnet for rotating said driving magnet and said magnetically coupled stirring magnet.

11. The photometer of claim 1 wherein said third optical means further includes lens means disposed within the path of said light transmitted through said aperture for focusing said light on said second photoelectric detector.

12. The photometer of claim 1 wherein said optical second axis defines an angle of 90° relative to the first axis.

13. The photometer of claim 1 wherein the rays of the incident beam scattered by the hydrosol through the aperture defines an angle of 2°.

* * * * *